United States Patent
Lawlor

(10) Patent No.: US 7,361,476 B2
(45) Date of Patent: Apr. 22, 2008

(54) METHIONYL TRNA SYNTHETASE POLYNUCLEOTIDES

(75) Inventor: Elizabeth Jane Lawlor, Malvern, PA (US)

(73) Assignee: Replidyne, Inc., Louisville, CO (US)

(*) Notice: Subject to any disclaimer, the term of this patent is extended or adjusted under 35 U.S.C. 154(b) by 0 days.

(21) Appl. No.: 11/169,087

(22) Filed: Jun. 28, 2005

(65) Prior Publication Data

US 2006/0063176 A1 Mar. 23, 2006

Related U.S. Application Data

(60) Continuation of application No. 10/606,607, filed on Jun. 26, 2003, now abandoned, which is a division of application No. 10/187,641, filed on Jul. 1, 2002, now abandoned, which is a continuation of application No. 10/025,189, filed on Dec. 19, 2001, now abandoned, which is a continuation of application No. 09/432,695, filed on Nov. 3, 1999, now abandoned, which is a division of application No. 08/844,059, filed on Apr. 18, 1997, now Pat. No. 6,001,601.

(30) Foreign Application Priority Data

Apr. 18, 1996 (GB) .................. 9607999.1

(51) Int. Cl.
*G01N 33/53* (2006.01)
*C12N 9/00* (2006.01)
*C12N 9/99* (2006.01)

(52) U.S. Cl. ................. 435/7.1; 435/183; 435/184

(58) Field of Classification Search ................. None
See application file for complete search history.

(56) References Cited

U.S. PATENT DOCUMENTS 5,801,013 A * 9/1998 Tao et al. ................. 435/69.1
6,001,601 A * 12/1999 Lawlor ..................... 435/69.3
6,320,051 B1  11/2001 Berge et al.

OTHER PUBLICATIONS

Alonso et al. (1990) Nucleic Acids Research 18(23):6771-77.
Branch (1998) TIBS, 23:45-50.
Calendar et al. (1966) Biochemistry 5(5):1681-1690.
Cassio and Waller (1970) FEBS Letters, 12:309.
Dorland's Illustrated Medical Dictionary, 27 Ed. W.B. Sauders Co., Harcourt Brace Jovanovich Inc. 1988, p. 95.
Hughes et al. (1980) FEBS Letters 122(2):322-324.
Kalogerakos et al. (1980) Biochemistry 19:3712.
Kohda et al. (1987) J. Biol. Chem. 262:558.
Mechulam et al. (1991) Nucleic Acids Research 19(13):3673-3681.
Meinnel et al. (1995) Am Soc for Microbiology Chapter 14, p. 251-292.
Menguito et al. (1993) Nucleic Acids Research 21(3): 615-620.
Nureki et al. (1991) Journal of Biological Chemistry, 266(5):3268-77.
Von der Haar et al. (1981) Angew. Chem. Int. Ed. Engl. 20(3):217-223.

* cited by examiner

*Primary Examiner*—Nancy Vogel
(74) *Attorney, Agent, or Firm*—Swanson & Bratschun, L.L.C.

(57) ABSTRACT

The invention provides metS polypeptides and DNA (RNA) encoding metS polypeptides and methods for producing such polypeptides by recombinant techniques. Also provided are methods for utilizing metS polypeptides to screen for antibacterial compounds.

5 Claims, No Drawings

METHIONYL TRNA SYNTHETASE POLYNUCLEOTIDES

RELATED APPLICATIONS

This application claims benefit of U.S. application Ser. No. 10/606,607, filed Jun. 26, 2003, entitled "Methionyl tRNA Synthetase Polynucleotides," now abandonded, which is a divisional of U.S. application Ser. No. 10/187,641, filed Jul. 1, 2002, now abandonded, which is a continuation of U.S. application Ser. No. 10/025,189 filed Dec. 19, 2001, now abandonded, which claims the benefit of U.S. application Ser. No. 09/432,695, filed Nov. 3, 1999, abandoned, which is a divisional of U.S. application Ser. No. 08/844,059, filed Apr. 18, 1997, now U.S. Pat. No. 6,001,601, which claims the benefit of U.K. Application Serial No. 9607999.1, filed Apr. 18, 1996, expired.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the methionyl tRNA synthetase family, hereinafter referred to as "metS".

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in fact, the genetic material was predicated on the work of Griffith and of Avery, Macleod and McCarty using this microbe. Despite the vast amount of research with *S. pneumoniae*, many questions concerning the virulence of this microbe remain. It is particularly preferred to employ Streptococcal genes and gene products as targets for the development of antibiotics.

The frequency of *Streptococcus pneumoniae* infections has risen dramatically in the past 20 years. This has been attributed to the emergence of multiply antibiotic resistant strains and an increasing population of people with weakened immune systems. It is no longer uncommon to isolate *Streptococcus pneumoniae* strains which are resistant to some or all of the standard antibiotics. This has created a demand for both new anti-microbial agents and diagnostic tests for this organism.

The t-RNA synthetases have a primary role in protein synthesis according to the following scheme:

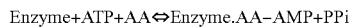

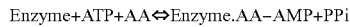

Enzyme.AA−AMP+t-RNA⇔Enzyme+AMP+AA−t-RNA in which AA is an amino acid.

Inhibition of this process leads to a reduction in the levels of charged t-RNA and this triggers a cascade of responses known as the stringent response, the result of which is the induction of a state of dormancy in the organism. As such selective inhibitors of bacterial t-RNA synthetase have potential as antibacterial agents. One example of such is mupirocin which is a selective inhibitor of isoleucyl t-RNA synthetase. Other t-RNA synthetases are now being examined as possible anti-bacterial targets, this process being greatly assisted by the isolation of the synthetase.

Clearly, there is a need for factors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known *Bacillus stearothermophilus* methionyl tRNA synthetase protein.

SUMMARY OF THE INVENTION

It is an object of the invention to provide polypeptides that have been identified as novel metS polypeptides by homology between the amino acid sequence set out in Table 1 [SEQ ID NO: 2] and a known amino acid sequence or sequences of other proteins such as *Bacillus stearothermophilus* methionyl tRNA synthetase protein.

It is a further object of the invention to provide polynucleotides that encode metS polypeptides, particularly polynucleotides that encode the polypeptide herein designated metS.

In a particularly preferred embodiment of the invention the polynucleotide comprises a region encoding metS polypeptides comprising the sequence set out in Table 1 [SEQ ID NO:1] which includes a full length gene, or a variant thereof.

In another particularly preferred embodiment of the invention there is a novel metS protein from *Streptococcus pneumoniae* comprising the amino acid sequence of Table 1 [SEQ ID NO:2], or a variant thereof.

In accordance with another aspect of the invention there is provided an isolated nucleic acid molecule encoding a mature polypeptide expressible by the *Streptococcus pneumoniae* 0100993 strain contained in the deposited strain.

A further aspect of the invention there are provided isolated nucleic acid molecules encoding metS, particularly *Streptococcus pneumoniae* metS, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of metS and polypeptides encoded thereby.

Another aspect of the invention there are provided novel polypeptides of *Streptococcus pneumoniae* referred to herein as metS as well as biologically, diagnostically, prophylactically, clinically or therapeutically useful variants thereof, and compositions comprising the same.

Among the particularly preferred embodiments of the invention are variants of metS polypeptide encoded by naturally occurring alleles of the metS gene.

In a preferred embodiment of the invention there are provided methods for producing the aforementioned metS polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing metS expression, treating disease, for example, otitis media, conjunctivitis, pneumonia, bacteremia, meningitis, sinusitis, pleural empyema and endocarditis, and most particularly meningitis, such as for example infection of cerebrospinal fluid, assaying genetic variation, and administering a metS polypeptide or polynucleotide to an organism to raise an immunological response against a bacteria, especially a Streptococcus pneumoniae bacteria.

In accordance with certain preferred embodiments of this and other aspects of the invention there are provided polynucleotides that hybridize to metS polynucleotide sequences, particularly under stringent conditions.

In certain preferred embodiments of the invention there are provided antibodies against metS polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided metS agonists and antagonists, preferably bacteriostatic or bacteriocidal agonists and antagonists.

In a further aspect of the invention there are provided compositions comprising a metS polynucleotide or a metS polypeptide for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). As an illustration, by a polynucleotide having a nucleotide sequence having at least, for example, 95% "identity" to a reference nucleotide sequence of SEQ ID NO: 1 it is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1-12 in *POSTTRANSLATIONAL COVALENT MODIFICATION OF PROTEINS,* B. C. Johnson, Ed., Academic Press, New York (1983); Seifter et al., *Meth. Enzymol.* 182:626-646 (1990) and Rattan et al., *Protein Synthesis: Posttranslational Modifications and Aging,* Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel metS polypeptides and polynucleotides as described in greater detail below. In particular, the invention relates to polypeptides and polynucleotides of a novel metS of *Streptococcus pneumoniae,* which is related by amino acid sequence homology to *Bacillus stearothermophilus* methionyl tRNA synthetase polypeptide. The invention relates especially to metS having the nucleotide and amino acid sequences set out in Table 1 [SEQ ID NO: 1] and Table 1 [SEQ ID NO: 2] respectively, and to the metS nucleotide sequences of the DNA in the deposited strain and amino acid sequences encoded thereby.

TABLE 1 metS Polynucleotide and Polypeptide Sequences

[SEQ ID NO:1]

(A) Sequences from *Streptococcus pneumoniae* metS polynucleotide sequence.

```
5'-1   ATGTCTGAAA AAAATTTTTA TATTACGACG CCGATTTACT ATCCATCTGG
  51   GAAACTTCAT ATCGGTTCTG CCTACACAAC TATCGCATGT GATGTCCTAG
 101   CACGTTACAA ACGCCTGATG GGNTACGATG TATTTTATCT GACAGGTCTT
 151   GATGAACATG GTCAGAAAAT CCAGCAGAAA GCGGAAGAAG CTGGTATTAC
 201   ACCTCAAGCC TATGTTGATG GAATGGCGGT TGGAGTTAAA GAACTCTGGC
 251   AATTACTAGA TATCTCATAC GATAAATTTA TCCGTACAAC CGATGACTAC
 301   CATGAAAAAG TTGTCGCACA GGTCTTTGAA CGCTTACTTG CTCAAGATGA
 351   TATCTACTTG GGTGAATACT CTGGTTGGTA TTCAGTATCA GACGAAGAAT
 401   TCTTTACAGA AAGCCAGCTG GCAGAAGTTT CCGTGATGA AGCTGGAAAT
 451   GTGACTGGTG GTATTGCTCC ATCAGGTCAT GAGGTTGAAT GGGTTTCTGA
 501   AGAATCATAC TTCCTTCGCC TTAGCAAATA CCAAGACCGT TTGGTCGAAT
 551   TTTTCAAAGC TCATCCTGAA TTTATCACGC CAGATGGTCG TCTTAATGAA
 601   ATGCTACGCA ACTTCATCGA GCCAGGTTTG AAGATTTGG CGGTATCTCG
 651   TACAACCTTT ACATGGGGAG TGCCTGTCCC ATCAAATCCA AAACACGTTG
 701   TCTACGTTTG GATTGATGCC CTTCTTAACT ATGCGACAGC TCTTGGCTAC
 751   GCTCAAGACG AACATGGTAA CTTTGACAAG TTCTGGAATG GAACAGTCTT
 801   CCATATGGTA GGAAAAGACA TCCTTCGCTT CCACTCTATC TACTGGCCAA
 851   TCCTTCTTAT GATGTTGGAT GTTAAATTAC CTGATCGTTT GATTGCCCAT
 901   GGTTGGTTTG TCATGAAAGA CGGAAAAATG TCTAAGTCAA AAGGGAATGT
 951   CGTTTACCCT GAAATGTTGG TAGAGCGTTA TGGACTAGAT CCACTTCGTT
1001   ACTACCTCAT GCGTAACCTT CCAGTTGGTT CAGACGGAAC CTTTACTCCT
1051   GAAGACTATG TCGGTCGTAT CAACTATGAA TTGGCTAATG ACCTTGGGAA
1101   CCTCCTTAAC CGTACGGTTT CCATGATTAA TAAGTACTTT GATGGACAAA
1151   TCCCTGCCTA TGTAGAAGGT GTGACTGAAT TTGATCATGT TCTTGCTGAA
1201   GTTGCAGAAA AATCAATCGC AGACTTCCAT ACACACATGG AAGCAGTTGA
1251   TTATCCACGT GCGCTTGAAG CAGTCTGGAC TCTGATCTCT CGTACCAATA
1301   AATACATCGA TGAGACTGCA CCATGGGTCT TGGACAAGGA TGAAGCTCTT
1351   CGTGACCAAT TGGCAAGTGT CATGAGCCAT TGGCAAGCCA GCATTCGTGT
1401   AGTTGCTCAC TTGATTGAAC CATTTATGAT GGAAACTAGT CGTGCAGTTT
1451   TGACTCAAAT TGGTTTGGAA GAAGTTTCTA GTCTTGAAAA CTTGAGTTTG
1501   GCTGACTTCC CAGCAGATGT GACTGTAGTT GCCAAAGGAA CACCTATCTT
1551   TCCACGTCTA AATATGGAAG AAGAAATCGC CTATATCAAG GAACAAATGG
1601   AAGGCAATAA ACCAGCAGTC GAAAAAGAAT GGAATCCGGA CGAAGTTGAG
1651   CTCAAACTAA ACAAGGATGA AATCAAGTTT GAAGACTTTG ACAAGGTTGA
1701   AATCCGTGTC GCAGAAGTCA AAGAAGTGTC TAAAGTAGAA GGTTCAGATA
1751   AGTTGCTTCA ATTCCGCTTG GATGCTGGTG ATGGAGAAGA TCGTCAGATT
1801   CTTTCAGGAA TTGCAAAATA CTATCCAAAT GAACAAGAAT TGGTCGGCAA
1851   GAAAGTTCAA ATCGTTGCTA ACCTCAAACC ACGTAAAATG ATGAAAAAAT
1901   ATGTCAGCCA GGGTATGATT CTCTCAGCTG AACATGATGG CAAATTAACC
1951   CTTCTCACAG TTGATCCAGC TGTACCAAAT GGAAGTGTGA TTGGGTAA-3'
```

[SEQ ID NO:2]

(B) metS polypeptide sequence deduced from the polynucleotide sequence in this table.

```
NH2-1  MSEKNFYITT PIYYPSGKLH IGSAYTTIAC DVLARYKRLM GYDVFYLTGL
  51   DEHGQKIQQK AEEAGITPQA YVDGMAVGVK ELWQLLDISY DKFIRTTDDY
 101   HEKVVAQVFE RLLAQDDIYL GEYSGWYSVS DEEFFTESQL AEVFRDEAGN
 151   VTGGIAPSGH EVEWVSEESY FLRLSKYQDR LVEFFKAHPE FITPDGRLNE
 201   MLRNFIEPGL EDLAVSRTTF TWGVPVPSNP KHVVYVWIDA LLNYATALGY
 251   AQDEHGNFDK FWNGTVFHMV GKDILRFHSI YWPILLMMLD VKLPDRLIAH
 301   GWFVMKDGKM SKSKGNVVYP EMLVERYGLD PLRYYLMRNL PVGSDGTFTP
 351   EDYVGRINYE LANDLGNLLN RTVSMINKYF DGQIPAYVEG VTEFDHVLAE
 401   VAEKSIADFH THMEAVDYPR ALEAVWTLIS RTNKYIDETA PWVLDKDEAL
 451   RDQLASVMSH WQASIRVVAH LIEPFMNETS RAVLTQIGLE EVSSLENLSL
 501   ADFPADVTVV AKGTPIFPRL NMEEEIAYIK EQMEGNKPAV EKEWNPDEVE
 551   LKLNKDEIKF EDFDKVEIRV AEVKEVSKVE GSDKLLQFRL DAGDGEDRQI
 601   LSGIAKYYPN EQELVGKKVQ IVANLKPRKM MKKYVSQGMI LSAEHDGKLT
 651   LLTVDPAVPN GSVIG-COOH
```

[SEQ ID NO:1]

(C) Polynucleotide sequence embodiments.

```
X-(R1)n-1  ATGTCTGAAA AAAATTTTTA TATTACGACG CCGATTTACT ATCCATCTGG
  51   GAAACTTCAT ATCGGTTCTG CCTACACAAC TATCGCATGT GATGTCCTAG
 101   CACGTTACAA ACGCCTGATG GGNTACGATG TATTTTATCT GACAGGTCTT
 151   GATGAACATG GTCAGAAAAT CCAGCAGAAA GCGGAAGAAG CTGGTATTAC
 201   ACCTCAAGCC TATGTTGATG GAATGGCGGT TGGAGTTAAA GAACTCTGGC
 251   AATTACTAGA TATCTCATAC GATAAATTTA TCCGTACAAC CGATGACTAC
 301   CATGAAAAAG TTGTCGCACA GGTCTTTGAA CGCTTACTTG CTCAAGATGA
 351   TATCTACTTG GGTGAATACT CTGGTTGGTA TTCAGTATCA GACGAAGAAT
 401   TCTTTACAGA AAGCCAGCTG GCAGAAGTTT CCGTGATGA AGCTGGAAAT
 451   GTGACTGGTG GTATTGCTCC ATCAGGTCAT GAGGTTGAAT GGGTTTCTGA
 501   AGAATCATAC TTCCTTCGCC TTAGCAAATA CCAAGACCGT TTGGTCGAAT
 551   TTTTCAAAGC TCATCCTGAA TTTATCACGC CAGATGGTCG TCTTAATGAA
 601   ATGCTACGCA ACTTCATCGA GCCAGGTTTG AAGATTTGG CGGTATCTCG
```

TABLE 1-continued metS Polynucleotide and Polypeptide Sequences

```
 651    TACAACCTTT ACATGGGAG  TGCCTGTCCC ATCAAATCCA AAACACGTTG
 701    TCTACGTTTG GATTGATGCC CTTCTTAACT ATGCGACAGC TCTTGGCTAC
 751    GCTCAAGACG AACATGGTAA CTTTGACAAG TTCTGGAATG GAACAGTCTT
 801    CCATATGGTA GGAAAAGACA TCCTTCGCTT CCACTCTATC TACTGGCCAA
 851    TCCTTCTTAT GATGTTGGAT GTTAAATTAC CTGATCGTTT GATTGCCCAT
 901    GGTTGGTTTG TCATGAAAGA CGGAAAAATG TCTAAGTCAA AAGGGAATGT
 951    CGTTTACCCT GAAATGTTGG TAGAGCGTTA TGGACTAGAT CCACTTCGTT
1001    ACTACCTCAT GCGTAACCTT CCAGTTGGTT CAGACGGAAC CTTTACTCCT
1051    GAAGACTATG TCGGTCGTAT CAACTATGAA TTGGCTAATG ACCTTGGGAA
1101    CCTCCTTAAC CGTACGGTTT CCATGATTAA TAAGTACTTT GATGGACAAA
1151    TCCCTGCCTA TGTAGAAGGT GTGACTGAAT TTGATCATGT TCTTGCTGAG
1201    GTTGCAGAAA AATCAATCGC AGACTTCCAT ACACACATGG AAGCAGTTGA
1251    TTATCCACGT GCGCTTGAAG CAGTCTGGAC TCTGATCTCT CGTACCAATA
1301    AATACATCGA TGAGACTGCA CCATGGGTCT TGGACAAGGA TGAAGCTCTT
1351    CGTGACCAAT TGGCAAGTGT CATGAGCCAT TGGCAAGCCA GCATTCGTGT
1401    AGTTGCTCAC TTGATTGAAC CATTTATGAT GGAAACTAGT CGTGCAGTTT
1451    TGACTCAAAT TGGTTTGGAA GAAGTTTCTA GTCTTGAAAA CTTGAGTTTG
1501    GCTGACTTCC CAGCAGATGT GACTGTAGTT GCCAAAGGAA CACCTATCTT
1551    TCCACGTCTA AATATGGAAG AAGAAATCGC CTATATCAAG GAACAAATGG
1601    AAGGCAATAA ACCAGCAGTC GAAAAAGAAT GGAATCCGGA CGAAGTTGAG
1651    CTCAAACTAA ACAAGGATGA AATCAAGTTT GAAGACTTTG ACAAGGTTGA
1701    AATCCGTGTC GCAGAAGTCA AAGAAGTGTC TAAAGTAGAA GGTTCAGATA
1751    AGTTGCTTCA ATTCCGCTTG GATGCTGGTG ATGGAGAAGA TCGTCAGATT
1801    CTTTCAGGAA TTGCAAAATA CTATCCAAAT GAACAAGAAT TGGTCGGCAA
1851    GAAAGTTCAA ATCGTTGCTA ACCTCAAACC ACGTAAAATG ATGAAAAAAT
1901    ATGTCAGCCA GGGTATGATT CTCTCAGCTG AACATGATGG CAAATTAACC
1951    CTTCTCACAG TTGATCCAGC TGTACCAAAT GGAAGTGTGA TTGGGTAA-(R₂)ₙ-Y
```
[SEQ ID NO:2]

(D) Polypeptide sequence embodiments

```
X-(R₁)ₙ-1   MSEKNFYITT PIYYPSGKLH IGSAYTTIAC DVLARYKRLM GYDVFYLTGL
  51        DEHGQKIQQK AEEAGITPQA YVDGMAVGVK ELWQLLDISY DKFIRTTDDY
 101        HEKVVAQVFE RLLAQDDIYL GEYSGWYSVS DEEFFTESQL AEVFRDEAGN
 151        VTGGIAPSGH EVEWVSEESY FLRLSKYQDR LVEFFKAHPE FITPDGRLNE
 201        MLRNFIEPGL EDLAVSRTTF TWGVPVPSNP KHVVYVWIDA LLNYATALGY
 251        AQDEHGNFDK FWNGTVFHMV GKDILRFHSI YWPILLMNLD VKLPDRLIAH
 301        GWFVMKDGKM SKSKGNVVYP EMLVERYGLD PLRYYLMRNL PVGSDGTFTP
 351        EDYVGRINYE LANDLGNLLN RTVSMINKYF DGQIPAYVEG VTEFDHVLAE
 401        VAEKSIADFH THMEAVDYPR ALEAVWTLIS RTNKYIDETA PWVLDKDEAL
 451        RDQLASVMSH WQASIRVVAH LIEPFMMETS RAVLTQIGLE EVSSLENLSL
 501        ADFPADVTVV AKGTPIFPRL NMEEEIAYIK EQMEGNKPAV EKEWNPDEVE
 551        LKLNKDEIKF EDFDKVEIRV AEVKEVSKVE GSDKLLQFRL DAGDGEDRQI
 601        LSGIAKYYPN EQELVGKKVQ IVANLKPRKM MKKYVSQGMI LSAEHDGKLT
 651        LLTVDPAVPN GSVIG-(R₂)ₙ-Y
```
[SEQ ID NO:3]

(E) Sequences from *Streptococcus pneumoniae* metS polynucleotide ORF sequence.

```
5'-1    CTCAAACTAA ACAAGGATGA AATCAAGTTT GAAGACTTTG ACAAGGTTGA
 51     AATCCGTGTC GCAGAAGTCA AAGAAGTGTC TAAAGTAGAA GGTTCAGATA
101     AGTTGCTTCA ATTCCGCTTG GATGCTGGTG ATGGAGAAGA TCGTCAGATT
151     CTTTCAGGAA TTGCAAAATA CTATCCAAAT GAACAAGAAT TGGTCGGCAA
201     GAAAGTTCAA ATCGTTGCTA ACCTCAAACC ACGTAAAATG ATGAAAAAAT
251     ATGTCAGCCA GGGTATGATT CTCTCAGCTG AACATGATGG CAAATTAACC
301     CTTCTCACAG TTGATCCAGC TGTACCAAAT GGAAGTGTGA TTGGGTAA-3'
```
[SEQ ID NO:4]

(F) metS polypeptide sequence deduced from the polynucleotide ORF sequence in this table.

```
NH₂-1   LKLNKDEIKF EDFDKVEIRV AEVKEVSKVE GSDKLLQFRL DAGDGEDRQI
  51    LSGIAKYYPN EQELVGKKVQ IVANLKPRKM MKKYVSQGMI LSAEHDGKLT
 101    LLTVDPAVPN GSVIG-COOH
```

DEPOSITED MATERIALS

A deposit containing a *Streptococcus pneumoniae* 0100993 strain has been deposited with the National Collections of Industrial and Marine Bacteria Ltd. (herein "NCIMB"), 23 St. Machar Drive, Aberdeen AB2 1RY, Scotland on 11 Apr. 1996 and assigned deposit number 40794. The deposit was described as *Streptococcus pneumoniae* 0100993 on deposit.

On 17 Apr. 1996 a *Streptococcus pneumoniae* 0100993 DNA library in *E. coli* was similarly deposited with the NCIMB and assigned deposit number 40800.

The *Streptococcus pneumoniae* strain deposit is referred to herein as "the deposited strain" or as "the DNA of the deposited strain."

The deposited strain contains the full length metS gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. § 112.

A license may be required to make, use or sell the deposited strain, and compounds derived therefrom, and no such license is hereby granted.

Polypeptides

The polypeptides of the invention include the polypeptide of Table 1 [SEQ ID NO:2] (in particular the mature polypeptide) as well as polypeptides and fragments, particularly those which have the biological activity of metS, and also those which have at least 70% identity to a polypeptide of Table 1 [SEQ ID NOS:2 and 4] or the relevant portion, preferably at least 80% identity to a polypeptide of Table 1 [SEQ ID NOS:2 and 4], and more preferably at least 90% similarity (more preferably at least 90% identity) to a polypeptide of Table 1 [SEQ ID NOS:2 and 4] and still more preferably at least 95% similarity (still more preferably at least 95% identity) to a polypeptide of Table 1 [SEQ ID NOS:2 and 4] and also include portions of such polypeptides with such portion of the polypeptide generally containing at least 30 amino acids and more preferably at least 50 amino acids.

The invention also includes polypeptides of the formula set forth in Table 1 (D) [SEQ ID NO:2] wherein, at the amino terminus, X is hydrogen, and at the carboxyl terminus, Y is hydrogen or a metal, $R_1$ and $R_2$ is any amino acid residue, and n is an integer between 1 and 1000. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with metS polypeptides fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of Table 1 [SEQ ID NOS:2 and 4], or of variants thereof, such as a continuous series of residues that includes the amino terminus, or a continuous series of residues that includes the carboxyl terminus. Degradation forms of the polypeptides of the invention in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of metS, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Streptococcus pneumoniae* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides

Another aspect of the invention relates to isolated polynucleotides, including the full length gene, that encode the metS polypeptide having a deduced amino acid sequence of Table 1 [SEQ ID NOS:2 and 4] and polynucleotides closely related thereto and variants thereof.

Using the information provided herein, such as a polynucleotide sequence set out in Table 1 [SEQ ID NOS:1 and 3], a polynucleotide of the invention encoding metS polypeptide may be obtained using standard cloning and screening methods, such as those for cloning and sequencing chromosomal DNA fragments from bacteria using *Streptococcus pneumoniae* 0100993 cells as starting material, followed by obtaining a full length clone. For example, to obtain a polynucleotide sequence of the invention, such as a sequence given in Table 1 [SEQ ID NOS:1 and 3], typically a library of clones of chromosomal DNA of *Streptococcus pneumoniae* 0100993 in *E. coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO:1] was discovered in a DNA library derived from *Streptococcus pneumoniae* 0100993.

The DNA sequence set out in Table 1 [SEQ ID NOS:1] contains an open reading frame encoding a protein having about the number of amino acid residues set forth in Table 1 [SEQ ID NOS:2] with a deduced molecular weight that can be calculated using amino acid residue molecular weight values well known in the art. The start codon of the DNA in Table 1 is nucleotide number 1 and last codon that encodes an amino acid is number 1995, the stop codon being the next codon following this last codon encoding an amino acid.

metS of the invention is structurally related to other proteins of the methionyl tRNA synthetase family, as shown by the results of sequencing the DNA encoding metS of the deposited strain. The protein exhibits greatest homology to *Bacillus stearothermophilus* methionyl tRNA synthetase protein among known proteins. metS of Table 1 [SEQ ID NO:2] has about 58% identity over its entire length and about 76% similarity over its entire length with the amino acid sequence of *Bacillus stearothermophilus* methionyl tRNA synthetase polypeptide.

The invention provides a polynucleotide sequence identical over its entire length to the coding sequence in Table 1 [SEQ ID NO:1]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci., USA 86: 821-824 (1989), or an HA tag (Wilson et al., Cell 37: 767 (1984). Polynucleotides of the invention also include, but are not limited to, polynucleotides comprising a structural gene and its naturally associated sequences that control gene expression.

A preferred embodiment of the invention is the polynucleotide of comprising nucleotide 1 to 1995 set forth in SEQ ID NO:1 of Table 1 which encodes the metS polypeptide.

The invention also includes polynucleotides of the formula set forth in Table 1 (C)[SEQ ID NO:1] wherein, at the 5' end of the molecule, X is hydrogen, and at the 3' end of the molecule, Y is hydrogen or a metal, $R_1$ and $R_2$ is any nucleic acid residue, and n is an integer between 1 and 1000. Any stretch of nucleic acid residues denoted by either R group, where R is greater than 1, may be either a heteropolymer or a homopolymer, preferably a heteropolymer.

The term "polynucleotide encoding a polypeptide" as used herein encompasses polynucleotides that include a sequence encoding a polypeptide of the invention, particularly a bacterial polypeptide and more particularly a polypeptide of the Streptococcus pneumoniae metS having the amino acid sequence set out in Table 1 [SEQ ID NO:2]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table 1 [SEQ ID NO:2]. Variants that are fragments of the polynucleotides of the invention may be used to synthesize full-length polynucleotides of the invention.

Further particularly preferred embodiments are polynucleotides encoding metS variants, that have the amino acid sequence of metS polypeptide of Table 1 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of metS.

Further preferred embodiments of the invention are polynucleotides that are at least 70% identical over their entire length to a polynucleotide encoding metS polypeptide having an amino acid sequence set out in Table 1 [SEQ ID NOS:2 and 4], and polynucleotides that are complementary to such polynucleotides. Alternatively, most highly preferred are polynucleotides that comprise a region that is at least 80% identical over its entire length to a polynucleotide encoding metS polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 1 [SEQ ID NO:1].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 or SEQ ID NO:3 under stringent hybridization conditions with a probe having the sequence of said polynucleotide sequence set forth in SEQ ID NO:1 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding metS and to isolate cDNA and genomic clones of other genes that have a high sequence similarity to the metS gene. Such probes generally will comprise at least 15 bases. Preferably, such probes will have at least 30 bases and may have at least 50 bases. Particularly preferred probes will have at least 30 bases and will have 50 bases or less.

For example, the coding region of the metS gene may be isolated by screening using the DNA sequence provided in SEQ ID NO: 1 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of SEQ ID NOS:1 and/or 2 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli,* streptomyces and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the metS polynucleotides of the invention for use as diagnostic reagents. Detection of metS in a eukaryote, particularly a mammal, and especially a human, will provide a diagnostic method for diagnosis of a disease. Eukaryotes (herein also "individual(s)"), particularly mammals, and especially humans, infected with an organism comprising the metS gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled metS polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science,* 230: 1242 (1985). Sequence changes at specific locations also may be revealed by nuclease protection assays, such as RNase and S1 protection or a chemical cleavage method. See, e.g., Cotton et al., *Proc. Natl. Acad. Sci., USA*, 85: 4397-4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR As an example, PCR primers complementary to a nucleic acid encoding metS can be used to identify and analyze mutations. Examples of representative primers are shown below in Table 2.

TABLE 2

Primers for amplification of metS polynucleotides

| SEQ ID NO | PRIMER SEQUENCE |
|---|---|
| 5 | 5'-ATGTCTGAAAAAAATTTTTATATT-3' |
| 6 | 5'-TTACCCAATCACACTTCCATTTGG-3' |

The invention further provides these primers with 1, 2, 3 or 4 nucleotides removed from the 5' and/or the 3' end. These primers may be used for, among other things, amplifying metS DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Streptococcus pneumoniae*, and most preferably otitis media, conjunctivitis, pneumonia, bacteremia, meningitis, sinusitis, pleural empyema and endocarditis, and most particularly meningitis, such as for example infection of cerebrospinal fluid, comprising determining from a sample derived from an individual a increased level of expression of polynucleotide having the sequence of Table 1 [SEQ ID NO: 1]. Increased or decreased expression of metS polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of metS protein compared to normal control tissue samples may be used to detect the presence of an infection, for example. Assay techniques that can be used to determine levels of a metS protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495-497 (1975); Kozbor et al., *Immunology Today* 4: 72 (1983); Cole et al., pg. 77-96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-metS or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against metS-polypeptide may be employed to treat infections, particularly bacterial infections and especially otitis media, conjunctivitis, pneumonia, bacteremia, meningitis, sinusitis, pleural empyema and endocarditis, and most particularly meningitis, such as for example infection of cerebrospinal fluid.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522-525 or Tempest et al., (1991) Biotechnology 9, 266-273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol. Chem. 1989: 264, 16985), coprecipitation of DNA with calcium phosphate (Benvenisty & Reshef, PNAS, 1986:83, 9551), encapsulation of DNA in various forms of liposomes (Kaneda et al., Science 1989:243, 375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

Antagonists and Agonists—Assays and Molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The invention also provides a method of screening compounds to identify those which enhance (agonist) or block (antagonist) the action of metS polypeptides or polynucleotides, particularly those compounds that are bacteriostatic and/or bacteriocidal. The method of screening may involve high-throughput techniques. For example, to screen for agonists or antagonists, a synthetic reaction mix, a cellular compartment, such as a membrane, cell envelope or cell wall, or a preparation of any thereof, comprising metS polypeptide and a labeled substrate or ligand of such polypeptide is incubated in the absence or the presence of a candidate molecule that may be a metS agonist or antagonist. The ability of the candidate molecule to agonize or antagonize the metS polypeptide is reflected in decreased binding of the labeled ligand or decreased production of product from such substrate. Molecules that bind gratuitously, i.e., without inducing the effects of metS polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in metS polynucleotide or polypeptide activity, and binding assays known in the art.

Another example of an assay for metS antagonists is a competitive assay that combines metS and a potential antagonist with metS-binding molecules, recombinant metS binding molecules, natural substrates or ligands, or substrate or ligand mimetics, under appropriate conditions for a competitive inhibition assay. metS can be labeled, such as by radioactivity or a colorimetric compound, such that the number of metS molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing metS-induced activities, thereby preventing the action of metS by excluding metS from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of metS.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block metS protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial metS proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat otitis media, conjunctivitis, pneumonia, bacteremia, meningitis, sinusitis, pleural empyema and endocarditis, and most particularly meningitis, such as for example infection of cerebrospinal fluid.

Vaccines

Another aspect of the invention relates to a method for inducing an immunological response in an individual, particularly a mammal which comprises inoculating the individual with metS, or a fragment or variant thereof, adequate to produce antibody and/or T cell immune response to protect said individual from infection, particularly bacterial infection and most particularly *Streptococcus pneumoniae* infection. Also provided are methods whereby such immunological response slows bacterial replication. Yet another aspect of the invention relates to a method of inducing immunological response in an individual which comprises delivering to such individual a nucleic acid vector to direct expression of metS, or a fragment or a variant thereof, for expressing metS, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise.

Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a metS or protein coded therefrom, wherein the composition comprises a recombinant metS or protein coded therefrom comprising DNA which codes for and expresses an antigen of said metS or protein coded therefrom. The immunological response may be used therapeutically or prophylactically and may take the form of antibody immunity or cellular immunity such as that arising from CTL or CD4+ T cells.

A metS polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Streptococcus pneumoniae* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Streptococcus pneumoniae* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain metS protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Streptococcus pneumoniae* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response. A suitable unit dose for vaccination is 0.5-5 microgram/kg of antigen, and such dose is preferably administered 1-3 times and with an interval of 1-3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

The polynucleotide having the DNA sequence given in SEQ ID NO:1 was obtained from a library of clones of chromosomal DNA of *Streptococcus pneumoniae* in *E. coli*. The sequencing data from two or more clones containing overlapping *Streptococcus pneumoniae* DNAs was used to construct the contiguous DNA sequence in SEQ ID NO:1. Libraries may be prepared by routine methods, for example:

Methods 1 and 2 Below.

Total cellular DNA is isolated from *Streptococcus pneumoniae* 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2 metS Characterization

The enzyme mediated incorporation of radiolabelled amino acid into tRNA may be measured by the aminoacylation method which measures amino acid-tRNA as trichloroacetic acid-precipitable radioactivity from radiolabelled amino acid in the presence of tRNA and ATP (Hughes J, Mellows G and Soughton S, 1980, FEBS Letters, 122:322-324). Thus inhibitors of methionyl tRNA synthetase can be detected by a reduction in the trichloroacetic acid precipitable radioactivity relative to the control. Alternatively the tRNA synthetase catalysed partial PPi/ATP exchange reaction which measures the formation of radiolabelled ATP from PPi can be used to detect methionyl tRNA synthetase inhibitors (Calender R & Berg P, 1966, Biochemistry, 5, 1681-1690).

What is claimed is:

1. A method for identifying compounds which interact with, and inhibit or activate an activity of, a polypeptide comprising SEQ ID NO: 2, wherein the polypeptide exhibits methionyl tRNA synthetase activity, the method comprising:
    contacting a composition comprising the polypeptide with the compound to be screened under conditions to permit interaction between the compound and the polypeptide to assess the interaction of the compound, wherein such interaction is assessed using a label capable of providing a detectable signal in response to the interaction of the polypeptide with the compound; and determining whether the compound interacts with, and activates or inhibits an activity of, the polypeptide by detecting the presence or absence of a signal generated from the interaction of the compound with the polypeptide.

2. The method of claim 1, wherein the polypeptide further comprises a heterologous amino acid sequence fused to SEQ ID NO:2.

3. The method of claim 2, wherein the polypeptide comprising SEQ ID NO:2 consists of the heterologous amino acid sequence fused to SEQ ID NO:2.

4. A method for identifying compounds which interact with, and inhibit or activate an activity of, a polypeptide comprising an amino acid sequence that comprises a fragment of SEQ ID NO:2 comprising at least 50 consecutive amino acids, the method comprising:

contacting a composition comprising the polypeptide with the compound to be screened under conditions to permit interaction between the compound and the polypeptide to assess the interaction of the compound, wherein such interaction is assessed using a label capable of providing a detectable signal in response to the interaction of the polypeptide with the compound; and determining whether the compound interacts with, and activates or inhibits an activity of, the polypeptide by detecting the presence or absence of a signal generated from the interaction of the compound with the polypeptide.

5. The method of claim 4, wherein the polypeptide further comprises a heterologous amino acid sequence fused to the fragment of SEQ ID NO:2.

* * * * *

SEQUENCE LISTING

<160> NUMBER OF SEQ ID NOS: 6

<210> SEQ ID NO 1
<211> LENGTH: 1998
<212> TYPE: DNA
<213> ORGANISM: Streptococcus pneumoniae
<220> FEATURE: unknown
<221> NAME/KEY:
<222> LOCATION: (123)
<223> OTHER INFORMATION: Where n can be a, c, t, or g

<400> SEQUENCE: 1

```
atgtctgaaa aaattttta tattacgacg ccgatttact atccatctgg gaaacttcat      60
atcggttctg cctacacaac tatcgcatgt gatgtcctag cacgttacaa acgcctgatg     120
ggntacgatg tattttatct gacaggtctt gatgaacatg gtcagaaaat ccagcagaaa     180
gcggaagaag ctggtattac acctcaagcc tatgttgatg aatggcggt tggagttaaa      240
gaactctggc aattactaga tatctcatac gataaattta ccgtacaac cgatgactac      300
catgaaaaag ttgtcgcaca ggtctttgaa cgcttacttg ctcaagatga tatctacttg    360
ggtgaatact ctggttggta ttcagtatca gacgaagaat tctttacaga aagccagctg    420
gcagaagttt tccgtgatga agctggaaat gtgactggtg gtattgctcc atcaggtcat    480
gaggttgaat gggtttctga agaatcatac ttccttcgcc ttagcaaata ccaagaccgt    540
ttggtcgaat ttttcaaagc tcatcctgaa tttatcacgc cagatggtcg tcttaatgaa    600
atgctacgca acttcatcga gccaggtttg gaagatttgg cggtatctcg tacaaccttt    660
acatggggag tgcctgtccc atcaaatcca aacacgttg tctacgtttg gattgatgcc     720
cttcttaact atgcgacagc tcttggctac gctcaagacg aacatggtaa ctttgacaag    780
ttctggaatg aacagtctt ccatatggta ggaaaagaca tccttcgctt ccactctatc     840
tactggccaa tccttcttat gatgttggat gttaaattac ctgatcgttt gattgcccat    900
ggttggtttg tcatgaaaga cggaaaaatg tctaagtcaa aagggaatgt cgtttaccct    960
gaaatgttgg tagagcgtta tggactagat ccacttcgtt actacctcat gcgtaacctt   1020
ccagttggtt cagacggaac ctttactcct gaagactatg tcggtcgtat caactatgaa   1080
ttggctaatg accttgggaa cctccttaac cgtacggttt ccatgattaa taagtacttt   1140
gatggacaaa tccctgccta tgtagaaggt gtgactgaat tgatcatgt tcttgctgag    1200
gttgcagaaa atcaatcgc agacttccat acacacatgg aagcagttga ttatccacgt    1260
gcgcttgaag cagtctggac tctgatctct cgtaccaata aatacatcga tgagactgca   1320
ccatgggtct tggacaagga tgaagctctt cgtgaccaat ggcaagtgt catgagccat    1380
tggcaagcca gcattcgtgt agttgctcac ttgattgaac catttatgat ggaaactagt   1440
cgtgcagttt tgactcaaat tggtttggaa gaagtttcta gtcttgaaaa acttgagtttg  1500
gctgacttcc cagcagatgt gactgtagtt gccaaggaa cacctatctt ccacgtcta    1560
aatatggaag aagaaatcgc ctatatcaag gaacaaatgg aagcaataa accagcagtc    1620
gaaaaagaat ggaatccgga cgaagttgag ctcaaactaa acaaggatga aatcaagttt   1680
gaagactttg acaaggttga aatccgtgtc gcagaagtca agaagtgtc taaagtagaa    1740
ggttcagata agttgcttca attccgcttg gatgctggtg atggagaaga tcgtcagatt   1800
ctttcaggaa ttgcaaaata ctatccaaat gaacaagaat tggtcggcaa gaaagttcaa   1860
atcgttgcta acctcaaacc acgtaaaatg atgaaaaaat atgtcagcca gggtatgatt   1920
```

-continued

```
ctctcagctg aacatgatgg caaattaacc cttctcacag ttgatccagc tgtaccaaat    1980
ggaagtgtga ttgggtaa                                                  1998
```

<210> SEQ ID NO 2
<211> LENGTH: 665
<212> TYPE: PRT
<213> ORGANISM: Streptococcus pneumoniae

<400> SEQUENCE: 2

| | | | | | | | | | | | | | | |
|---|---|---|---|---|---|---|---|---|---|---|---|---|---|---|
| Met | Ser | Glu | Lys | Asn | Phe | Tyr | Ile | Thr | Thr | Pro | Ile | Tyr | Tyr | Pro | Ser |
| 1 | | | | 5 | | | | | 10 | | | | | 15 | |

| Gly | Lys | Leu | His | Ile | Gly | Ser | Ala | Tyr | Thr | Thr | Ile | Ala | Cys | Asp | Val |
|---|---|---|---|---|---|---|---|---|---|---|---|---|---|---|---|
| | | | | 20 | | | | | 25 | | | | | 30 | |

| Leu | Ala | Arg | Tyr | Lys | Arg | Leu | Met | Gly | Tyr | Asp | Val | Phe | Tyr | Leu | Thr |
|---|---|---|---|---|---|---|---|---|---|---|---|---|---|---|---|
| | | 35 | | | | | 40 | | | | | 45 | | | |

| Gly | Leu | Asp | Glu | His | Gly | Gln | Lys | Ile | Gln | Gln | Lys | Ala | Glu | Glu | Ala |
|---|---|---|---|---|---|---|---|---|---|---|---|---|---|---|---|
| | 50 | | | | | 55 | | | | | 60 | | | | |

| Gly | Ile | Thr | Pro | Gln | Ala | Tyr | Val | Asp | Gly | Met | Ala | Val | Gly | Val | Lys |
|---|---|---|---|---|---|---|---|---|---|---|---|---|---|---|---|
| 65 | | | | | 70 | | | | | 75 | | | | | 80 |

| Glu | Leu | Trp | Gln | Leu | Leu | Asp | Ile | Ser | Tyr | Asp | Lys | Phe | Ile | Arg | Thr |
|---|---|---|---|---|---|---|---|---|---|---|---|---|---|---|---|
| | | | | 85 | | | | | 90 | | | | | 95 | |

| Thr | Asp | Asp | Tyr | His | Glu | Lys | Val | Val | Ala | Gln | Val | Phe | Glu | Arg | Leu |
|---|---|---|---|---|---|---|---|---|---|---|---|---|---|---|---|
| | | | | 100 | | | | | 105 | | | | | 110 | |

| Leu | Ala | Gln | Asp | Asp | Ile | Tyr | Leu | Gly | Glu | Tyr | Ser | Gly | Trp | Tyr | Ser |
|---|---|---|---|---|---|---|---|---|---|---|---|---|---|---|---|
| | | 115 | | | | | 120 | | | | | 125 | | | |

| Val | Ser | Asp | Glu | Glu | Phe | Phe | Thr | Glu | Ser | Gln | Leu | Ala | Glu | Val | Phe |
|---|---|---|---|---|---|---|---|---|---|---|---|---|---|---|---|
| | 130 | | | | | 135 | | | | | 140 | | | | |

| Arg | Asp | Glu | Ala | Gly | Asn | Val | Thr | Gly | Gly | Ile | Ala | Pro | Ser | Gly | His |
|---|---|---|---|---|---|---|---|---|---|---|---|---|---|---|---|
| 145 | | | | | 150 | | | | | 155 | | | | | 160 |

| Glu | Val | Glu | Trp | Val | Ser | Glu | Glu | Ser | Tyr | Phe | Leu | Arg | Leu | Ser | Lys |
|---|---|---|---|---|---|---|---|---|---|---|---|---|---|---|---|
| | | | | 165 | | | | | 170 | | | | | 175 | |

| Tyr | Gln | Asp | Arg | Leu | Val | Glu | Phe | Phe | Lys | Ala | His | Pro | Glu | Phe | Ile |
|---|---|---|---|---|---|---|---|---|---|---|---|---|---|---|---|
| | | | 180 | | | | | 185 | | | | | 190 | | |

| Thr | Pro | Asp | Gly | Arg | Leu | Asn | Glu | Met | Leu | Arg | Asn | Phe | Ile | Glu | Pro |
|---|---|---|---|---|---|---|---|---|---|---|---|---|---|---|---|
| | | 195 | | | | | 200 | | | | | 205 | | | |

| Gly | Leu | Glu | Asp | Leu | Ala | Val | Ser | Arg | Thr | Thr | Phe | Thr | Trp | Gly | Val |
|---|---|---|---|---|---|---|---|---|---|---|---|---|---|---|---|
| | 210 | | | | | 215 | | | | | 220 | | | | |

| Pro | Val | Pro | Ser | Asn | Pro | Lys | His | Val | Val | Tyr | Val | Trp | Ile | Asp | Ala |
|---|---|---|---|---|---|---|---|---|---|---|---|---|---|---|---|
| 225 | | | | | 230 | | | | | 235 | | | | | 240 |

| Leu | Leu | Asn | Tyr | Ala | Thr | Ala | Leu | Gly | Tyr | Ala | Gln | Asp | Glu | His | Gly |
|---|---|---|---|---|---|---|---|---|---|---|---|---|---|---|---|
| | | | | 245 | | | | | 250 | | | | | 255 | |

| Asn | Phe | Asp | Lys | Phe | Trp | Asn | Gly | Thr | Val | Phe | His | Met | Val | Gly | Lys |
|---|---|---|---|---|---|---|---|---|---|---|---|---|---|---|---|
| | | | | 260 | | | | | 265 | | | | | 270 | |

| Asp | Ile | Leu | Arg | Phe | His | Ser | Ile | Tyr | Trp | Pro | Ile | Leu | Leu | Met | Met |
|---|---|---|---|---|---|---|---|---|---|---|---|---|---|---|---|
| | | | 275 | | | | | 280 | | | | | 285 | | |

| Leu | Asp | Val | Lys | Leu | Pro | Asp | Arg | Leu | Ile | Ala | His | Gly | Trp | Phe | Val |
|---|---|---|---|---|---|---|---|---|---|---|---|---|---|---|---|
| | 290 | | | | | 295 | | | | | 300 | | | | |

| Met | Lys | Asp | Gly | Lys | Met | Ser | Lys | Ser | Lys | Gly | Asn | Val | Val | Tyr | Pro |
|---|---|---|---|---|---|---|---|---|---|---|---|---|---|---|---|
| 305 | | | | | 310 | | | | | 315 | | | | | 320 |

| Glu | Met | Leu | Val | Glu | Arg | Tyr | Gly | Leu | Asp | Pro | Leu | Arg | Tyr | Tyr | Leu |
|---|---|---|---|---|---|---|---|---|---|---|---|---|---|---|---|
| | | | | 325 | | | | | 330 | | | | | 335 | |

| Met | Arg | Asn | Leu | Pro | Val | Gly | Ser | Asp | Gly | Thr | Phe | Thr | Pro | Glu | Asp |
|---|---|---|---|---|---|---|---|---|---|---|---|---|---|---|---|
| | | | 340 | | | | | 345 | | | | | 350 | | |

```
Tyr Val Gly Arg Ile Asn Tyr Glu Leu Ala Asn Asp Leu Gly Asn Leu
            355                 360                 365

Leu Asn Arg Thr Val Ser Met Ile Asn Lys Tyr Phe Asp Gly Gln Ile
    370                 375                 380

Pro Ala Tyr Val Glu Gly Val Thr Glu Phe Asp His Val Leu Ala Glu
385                 390                 395                 400

Val Ala Glu Lys Ser Ile Ala Asp Phe His Thr His Met Glu Ala Val
                405                 410                 415

Asp Tyr Pro Arg Ala Leu Glu Ala Val Trp Thr Leu Ile Ser Arg Thr
            420                 425                 430

Asn Lys Tyr Ile Asp Glu Thr Ala Pro Trp Val Leu Asp Lys Asp Glu
        435                 440                 445

Ala Leu Arg Asp Gln Leu Ala Ser Val Met Ser His Trp Gln Ala Ser
    450                 455                 460

Ile Arg Val Val Ala His Leu Ile Glu Pro Phe Met Met Glu Thr Ser
465                 470                 475                 480

Arg Ala Val Leu Thr Gln Ile Gly Leu Glu Glu Val Ser Ser Leu Glu
                485                 490                 495

Asn Leu Ser Leu Ala Asp Phe Pro Ala Asp Val Thr Val Val Ala Lys
            500                 505                 510

Gly Thr Pro Ile Phe Pro Arg Leu Asn Met Glu Glu Ile Ala Tyr
        515                 520                 525

Ile Lys Glu Gln Met Glu Gly Asn Lys Pro Ala Val Glu Lys Glu Trp
    530                 535                 540

Asn Pro Asp Glu Val Glu Leu Lys Leu Asn Lys Asp Glu Ile Lys Phe
545                 550                 555                 560

Glu Asp Phe Asp Lys Val Glu Ile Arg Val Ala Glu Val Lys Glu Val
                565                 570                 575

Ser Lys Val Glu Gly Ser Asp Lys Leu Leu Gln Phe Arg Leu Asp Ala
            580                 585                 590

Gly Asp Gly Glu Asp Arg Gln Ile Leu Ser Gly Ile Ala Lys Tyr Tyr
        595                 600                 605

Pro Asn Glu Gln Glu Leu Val Gly Lys Lys Val Gln Ile Val Ala Asn
    610                 615                 620

Leu Lys Pro Arg Lys Met Met Lys Lys Tyr Val Ser Gln Gly Met Ile
625                 630                 635                 640

Leu Ser Ala Glu His Asp Gly Lys Leu Thr Leu Leu Thr Val Asp Pro
                645                 650                 655

Ala Val Pro Asn Gly Ser Val Ile Gly
            660                 665

<210> SEQ ID NO 3
<211> LENGTH: 348
<212> TYPE: DNA
<213> ORGANISM: Streptococcus pneumoniae

<400> SEQUENCE: 3
ctcaaactaa acaaggatga aatcaagttt gaagactttg acaaggttga aatccgtgtc    60
gcagaagtca aagaagtgtc taaagtagaa ggttcagata agttgcttca attccgcttg   120
gatgctggtg atggagaaga tcgtcagatt ctttcaggaa ttgcaaaata ctatccaaat   180
```

-continued

```
gaacaagaat tggtcggcaa gaaagttcaa atcgttgcta acctcaaacc acgtaaaatg    240
atgaaaaaat atgtcagcca gggtatgatt ctctcagctg aacatgatgg caaattaacc    300
cttctcacag ttgatccagc tgtaccaaat ggaagtgtga ttgggtaa                 348
```

<210> SEQ ID NO 4
<211> LENGTH: 115
<212> TYPE: PRT
<213> ORGANISM: Streptococcus pneumoniae

<400> SEQUENCE: 4

```
Leu Lys Leu Asn Lys Asp Glu Ile Lys Phe Glu Asp Phe Asp Lys Val
 1               5                  10                  15

Glu Ile Arg Val Ala Glu Val Lys Glu Val Ser Lys Val Glu Gly Ser
            20                  25                  30

Asp Lys Leu Leu Gln Phe Arg Leu Asp Ala Gly Asp Gly Glu Asp Arg
        35                  40                  45

Gln Ile Leu Ser Gly Ile Ala Lys Tyr Tyr Pro Asn Glu Gln Glu Leu
    50                  55                  60

Val Gly Lys Lys Val Gln Ile Val Ala Asn Leu Lys Pro Arg Lys Met
65                  70                  75                  80

Met Lys Lys Tyr Val Ser Gln Gly Met Ile Leu Ser Ala Glu His Asp
                85                  90                  95

Gly Lys Leu Thr Leu Leu Thr Val Asp Pro Ala Val Pro Asn Gly Ser
            100                 105                 110

Val Ile Gly
        115
```

<210> SEQ ID NO 5
<211> LENGTH: 24
<212> TYPE: DNA
<213> ORGANISM: Streptococcus pneumoniae

<400> SEQUENCE: 5

```
atgtctgaaa aaattttta tatt                                             24
```

<210> SEQ ID NO 6
<211> LENGTH: 24
<212> TYPE: DNA
<213> ORGANISM: Streptococcus pneumoniae

<400> SEQUENCE: 6

```
ttacccaatc acacttccat ttgg                                            24
```